United States Patent [19]
Doyle

[11] Patent Number: 5,054,920
[45] Date of Patent: Oct. 8, 1991

[54] INTERNAL REFLECTANCE CELL HAVING IMPROVED SAMPLE FLOW GEOMETRY

[75] Inventor: Walter M. Doyle, Laguna Beach, Calif.

[73] Assignee: Axiom Analytical, Inc., Laguna Beach, Calif.

[21] Appl. No.: 424,150

[22] Filed: Oct. 10, 1989

[51] Int. Cl.⁵ ..................... G01N 21/09; G01N 21/41
[52] U.S. Cl. ..................... 356/246; 356/133; 356/244
[58] Field of Search ............... 356/244, 246, 300, 133; 250/252.1, 338.1, 339, 353

[56] References Cited

U.S. PATENT DOCUMENTS 3,726,599  4/1973  Neary .................................. 356/246

FOREIGN PATENT DOCUMENTS 0154942  6/1988  Japan .................................. 356/133

*Primary Examiner*—Vincent P. McGraw
*Assistant Examiner*—LaCharles P. Keesee
*Attorney, Agent, or Firm*—Thomas J. Plante

[57] ABSTRACT

An ATR sample cell is disclosed, of the type incorporating a circular internal reflectance crystal. A flowing liquid sample has input and output ports in the IRE housing, or cell, which are offset from the axis of the circular IRE (or rod) sufficiently to direct the flow of liquid against the internal wall (usually stainless steel) of the flow jacket, rather than against the IRE. This tends to create a helical flow path from the input port at one end of the housing to the output port at the other end of the housing. In order to further control the sample flow path, and augment the spiraling effect, two further improvements are disclosed. The structure through which the sample material enters the sample chamber surrounding the IRE is designed to establish a spiraling motion of the liquid flow before it enters the sample chamber. Also, the inner cylindrical wall of the metal housing has a groove which forms a helical path from the input to the output end.

9 Claims, 7 Drawing Sheets

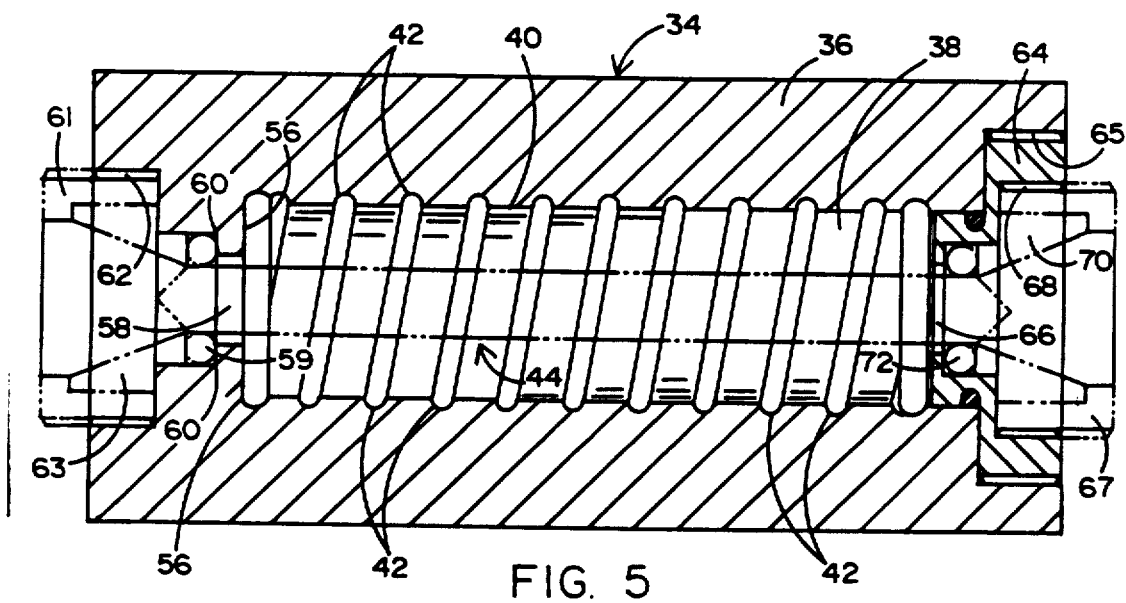
FIG. 5
FIG. 6
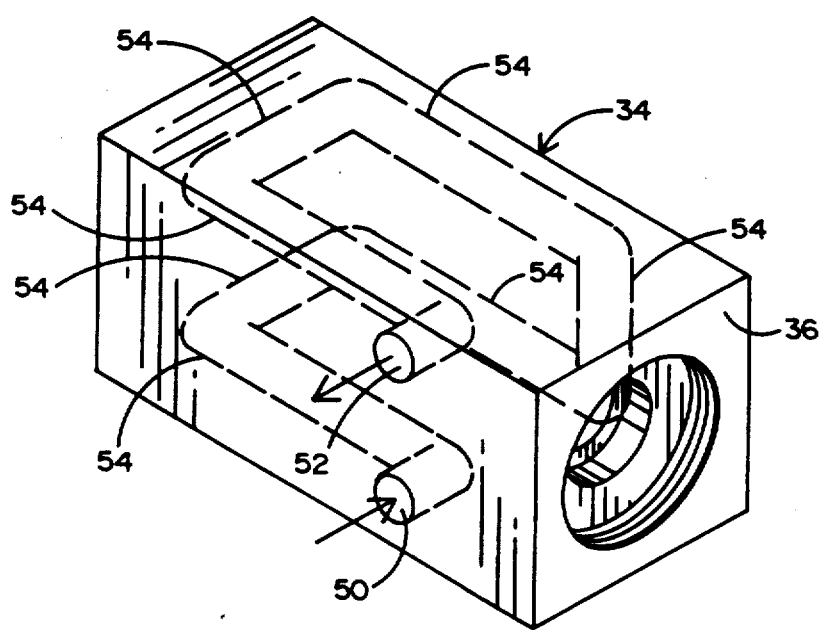

INTERNAL REFLECTANCE CELL HAVING IMPROVED SAMPLE FLOW GEOMETRY

BACKGROUND OF THE INVENTION

This invention relates to devices of the type in which liquid samples are analyzed by causing infrared radiation (IR) inside a transparent optical element to be partially absorbed by a liquid sample in which the element is immersed. The optical elements, formed of such materials as zinc selenide, germanium, etc., are often referred to as internal reflectance elements, and the units inside which they interface with the sample are often referred to as attenuated total reflectance (ATR) sample cells.

The present invention is primarily concerned with ATR cells in which the internal reflecting element (IRE) is circular in cross-section. The optical aspects and advantages of such circular internal reflectance (CIR) devices are discussed in detail in U.S. application Ser. No. 312,130, which was filed Feb. 17, 1989, and which has the same assignee as the present application.

Experience with CIR cells has uncovered certain problems of a mechanical, rather than optical, nature.

Although CIR cells are widely used to analyze both stationary and flowing liquids, a number of problems have been encountered with the flow jacket, or housing, designs being used. For one thing, the liquid flow velocity varies significantly from region to region in the sample cell. In fact, there are often regions referred to as "dead volume", in which the liquid flow rate is low and, as a result, sample material tends to accumulate. Often this material is not fully removed when the cell is flushed out with a solvent. This leads to spurious bands in the spectra of subsequent samples.

A second problem occurs when a cell is being used for the analysis of continuously flowing substances, but where either the flow rate is low or the sample is quite viscous. In such situations, the progressive build up of sample material in the cell can lead not only to an improper spectral time history of the process, but also in some cases to clogging of the cell.

A third problem occur when the flowing liquid to be analyzed contains catalysts or other abrasives. These can gradually abrade the relatively soft internal reflectance element (IRE), leading to a progressive decrease in IR transmission. This problem is exacerbated by the fact that the liquid input to the cell in prior designs is directed against the surface of the IRE.

SUMMARY OF THE INVENTION

In the present invention, the flowing liquid sample has input and output ports in the IRE housing, or cell, which are offset from the axis of the circular IRE (or rod) sufficiently to direct the flow of liquid against the internal wall (usually stainless steel) of the flow jacket, rather than against the IRE. This tends to create a spiraling flow path from the input port at one end of the housing to the output port at the other end of the housing.

In order to further control the sample flow path, and augment the spiraling effect, two further improvements are proposed. The structure through which the sample material enters the sample chamber surrounding the IRE is designed to establish a spiraling motion of the liquid flow before it enters the sample chamber. Also, the inner cylindrical wall of the metal housing has a helical groove which forms a helical path from the input to the output end.

The benefits obtained are: (1) minimizing abrasion of the internal reflectance element; (2) eliminating dead volume by using the helical flow path to insure that moving liquid reaches all areas of the cell; (3) increasing the flow distance and hence flow velocity of molecules in the sample, thus minimizing sample build up; and (4) directing any abrasive solid particles toward the outer wall of the chamber (rather than the IRE), due to the centrifugal effect of the helical flow.

The benefits of the present invention are clearly enhanced by use with a circular cross-section IRE element.

BRIEF DESCRIPTION OF THE DRAWINGS

FIG. 5 is a cross-section taken through the sample cell, with the IRE and its related optical elements shown in phantom;

FIG. 6 is an isometric exterior view of the sample cell, showing with dashed lines the flow channel of coolant fluid, which is used to maintain the desired temperature level of the sample cell;

DETAILED DESCRIPTION OF SPECIFIC EMBODIMENTS

Figure 1:
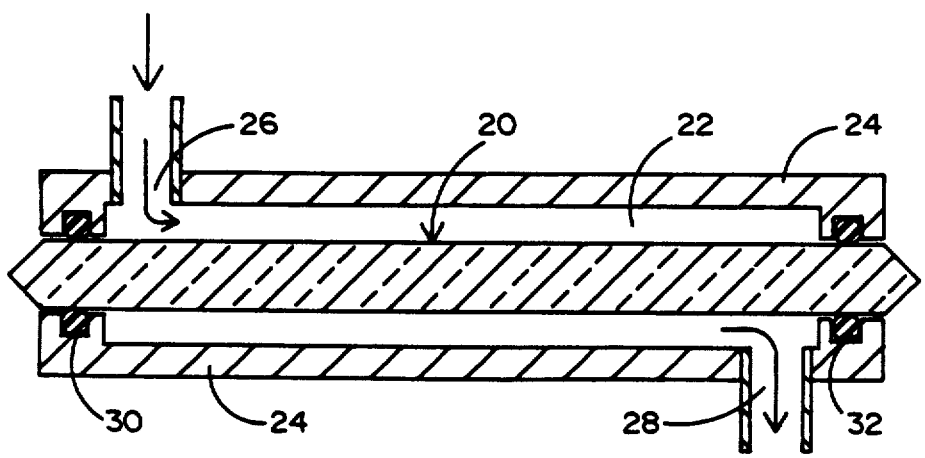
FIG. 1 is a cross-section taken through an enclosed sample chamber, or cell, of a prior art device having a circular cross-section IRE.

As background, attention is called to the previous structure shown in FIG. 1. A circular cross-section IRE 20 extends through a sample chamber 22 formed inside a housing, or jacket 24. Sample fluid enters through an inlet port 26, and exits through an outlet port 28. The fluid in chamber 22 is sealed from the optical portion of the system by O-ring seals 30 and 32, which are located at opposite ends of IRE 20, and which are in sealing engagement with the periphery of the IRE.

Radiation (infrared) is introduced at one end of IRE 20 and exits at the other end of the IRE. The radiation is reflected back and forth inside the IRE, and is modulated by partial absorption in the sample. A detailed description of the radiation characteristics of an IRE of the type shown is contained in application Ser. No. 312,130, referred to above. The disclosure of that application is incorporated herein by reference, in order to supply further details. In application Ser. No. 312,130, radiation is reflected at each end of IRE 20 by means of a concave conical reflector. Various other radiation-directing structures are compatible with the present invention, including that disclosed in Sting U.S. Pat. No. 4,595,833.

The present invention is concerned with the flow of sample fluid (liquid) in the chamber surrounding the IRE. A preferred embodiment of an improved sample cell 34 is the structure shown in FIGS. 2–8. It comprises a stainless steel housing, or jacket, 36 having a cylindrical bore which provides a sample chamber 38 (FIGS. 4 and 5). The housing 36 may, as shown, have a square cross-section. The wall 40 of sample chamber 38 has a continuous helical groove 42 formed therein.

Figure 2:
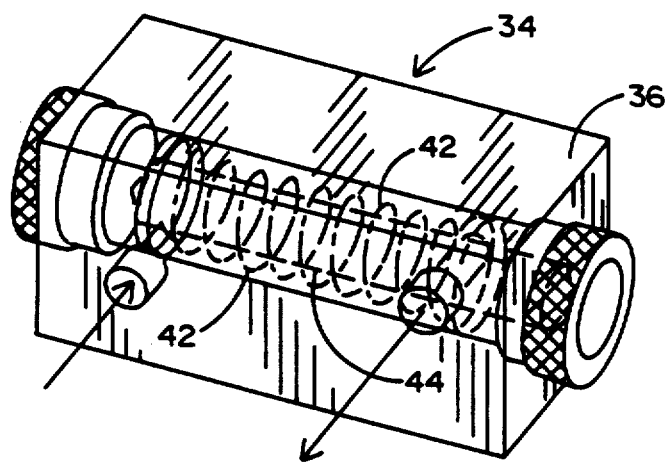
FIG. 2 is an isometric exterior view of a sample cell showing schematically the concepts of the present invention.

An internal reflectance element (IRE), or rod, similar to IRE 20 in FIG. 1, is located in the center of chamber 38 and extends from end to end of the chamber. FIG. 2 illustrates the spatial relationship of an IRE 44 and the helical groove 42 cut in the chamber wall. The longitudinal axes of IRE 44 and of chamber 38 are colinear. Thus the annular space between chamber wall 40 and the periphery of IRE 44 has a consistent width from end to end of the chamber, except for the helical groove 42.

Figure 3:
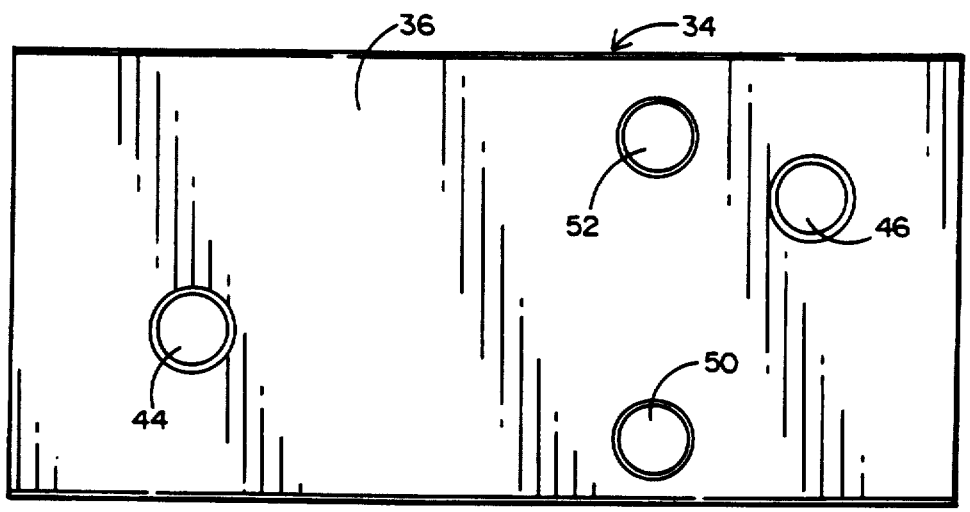
FIG. 3 is an exterior side view showing relative locations of certain ports in the sample cell of FIG. 2.
Figure 4:
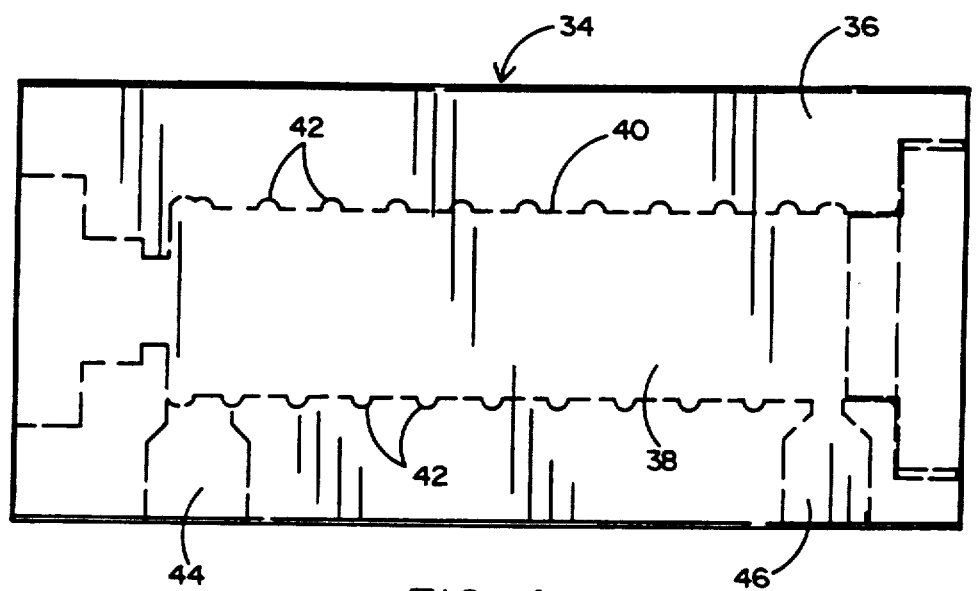
FIG. 4 is another side view of the sample cell, in which flow-directing grooves in the cell interior are shown in dashed lines.

As best seen in FIG. 3, a sample input port 44 is located below the longitudinal axis of chamber 38; and a sample output port 46 is located above the longitudinal axis of chamber 38. This location of ports 44 and 46 causes the entering and exiting sample flow to pass between the IRE periphery and the chamber wall 40.

Therefore, the input flow of the sample is directed against the stainless steel wall 40, rather than the relatively soft IRE. Also, the offset sample input port 44 initiates a generally helical motion around the IRE as the sample flows through the annular chamber toward the output port 46.

In order to augment this helical flow, the helical groove 42 is used to provide a "rifling" effect, i.e., the sample fluid tends to move in a helical path around the axis of symmetry of chamber 38.

The operation of the new ATR flow geometry can be understood by considering the movement of individual molecules, under the assumption that there is laminar flow entering the ATR cell, i.e., the molecules entering the cell are assumed to be traveling along straight streamlines. In this case, the behavior of a molecule can be predicted by a simple model which requires only that energy and momentum be conserved.

Consider the motion of an individual molecule in the new flow cell under the simplifying assumption that its primary interactions are with the wall of the cell rather than with other molecules that have already been deflected. Since the inlet to the cell is offset from the axis, the molecule will strike the wall at a fairly large angle of incidence. In a collision between a small moving object and a much larger stationary object, i.e., the molecule colliding with the wall, a negligible amount of energy is transferred to the larger object. The primary effect of the collision is to deflect the small object (molecule) along a new "mirror image" path, with no measurable change in the magnitude of its momentum.

Each molecule will experience several reflections at the wall while circling the periphery of the cell in a plane containing the input flow direction. After completing its first trip around the circumference, the molecule will collide with molecules currently entering the cell. The net effect of many such collisions is to slightly deflect the circling stream so that, on its second revolution, it follows a path parallel to the input stream. Once a down stream pitch has been established by these collisions, this pitch should be maintained on successive revolutions until the molecule reaches the output orifice.

The key assumption is that a given molecule or group of molecules will tend to behave in such a way as to conserve the magnitude of its momentum, even though its direction of motion will be changed by collisions with the wall. Since mass is fixed, this means that the magnitude of velocity will be constant. According to Bernoulli's principal, the velocity of a flowing liquid stream will remain constant only if its cross-sectional area is constant. Since constant velocity is a normal condition in the absence of turbulence, the pitch of the helical flow will automatically be adjusted so that the cross sectional area corresponding to one revolution around the cell is approximately equal to the area of the input orifice.

From the foregoing discussion, it can be seen that use of the helical groove 42 is not essential to the present invention. But the groove 42 should improve performance by helping to guide the flow along the desired path. This should be especially important during the first circuit around the cell. The groove 42 will begin to deflect the stream to one side before it makes a complete circuit back to the input orifice. This should minimize the chance that the interaction with the input flow would set up a turbulent condition. Typically, 10% of the total sample flow will occur in groove 42.

The generally helical motion of the sample liquid provides several major benefits in the analytical process, as summarized above:

1. Offsetting the input port minimizes abrasion of the IRE by the input stream.
2. The helical flow path eliminates dead volume by insuring that all areas of the sample cell are exposed to moving liquid.
3. Helical flow greatly increases the distance that a given liquid molecule travels in passing through the sample cell. If this situation is compared to a sample cell having the same volume but lacking the helical path, it will be clear that, because a given molecule must pass through the sample cell volume in a fixed amount of time, the new design will result in a much greater flow velocity, insuring that no sample buildup takes place.
4. The helical flow creates a centrifugal effect. Since any solid particles will generally be more massive than the surrounding liquid, they will tend to move toward the outer wall of the sample cell and away from the IRE, thus reducing potential abrasion of the IRE.

FIG. 6 illustrates a flow path formed in metal jacket 36, through which cooling fluid may be moved in order to maintain the desired temperature of the sample cell. Cooling fluid is shown entering through a port 50 and exiting through a port 52. Both ports are also seen in FIG. 3. The cooling fluid is separated from the sample fluid by the body of metal jacket 36. An extensive flow path 54, as shown in FIG. 6, may be established by boring several passages into the jacket 36, and capping the bored passages at the openings (not shown) through which the boring tool enters.

Figure 7:
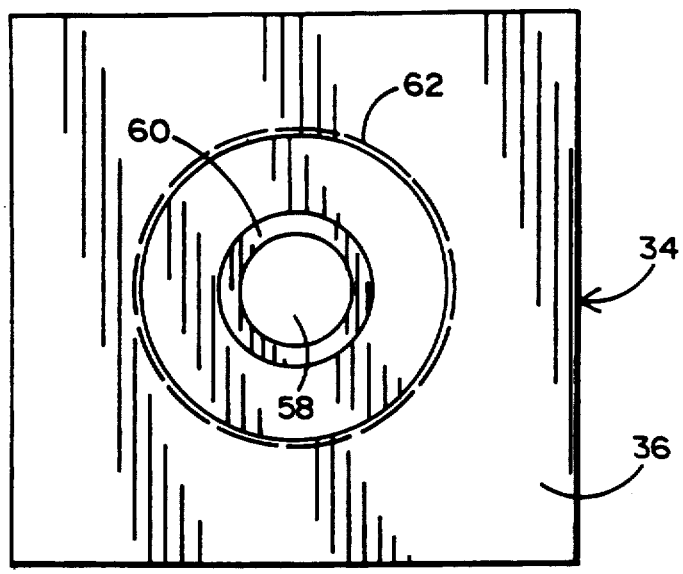
FIGS. 7 and 8 are opposite end views of the sample cell housing, or jacket, as they appear before insertion of the optical elements, the O-rings which seal the IRE chamber, and the annular threaded retaining members.
Figure 8:
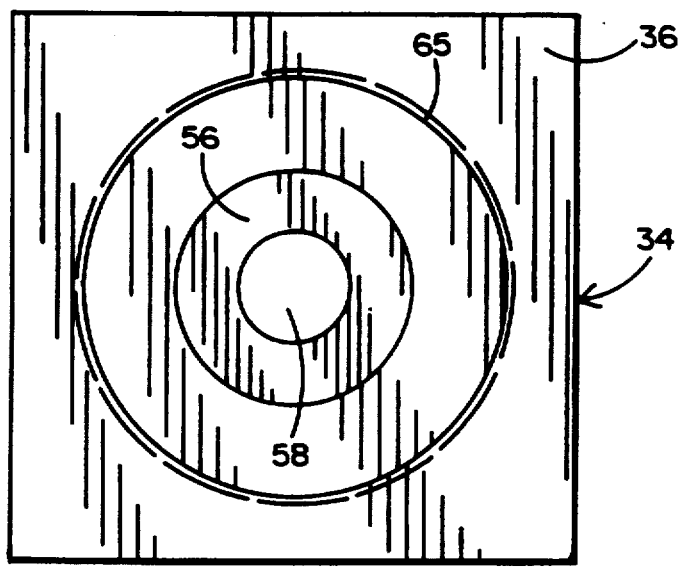

In forming the sample chamber in the metal jacket 36, a bore having the diameter of the chamber wall 40 may be formed from the right end of the jacket 36, as seen in FIGS. 5, 7 and 8. The bore ends at an end wall 56, having an opening 58 therethrough (see FIG. 8). In FIG. 5, the optical elements (IRE and conical reflectors) are shown in phantom. An O-ring seal 59 is held against a shoulder 60 formed in the jacket. An externally threaded annular nut 61 may be secured to the internally threaded opening 62 at the left end of the jacket. That nut holds in place a reflecting cone 63, which engages O-ring 59 and also engages IRE 44 peripherally near the left end of the IRE. At the right end of the jacket, an additional, larger annular nut 64, secured to an internally threaded opening 65, is required (a) to bring the original jacket opening down to a size which will provide a central opening 66 matching the diameter of opening 58, and (b) to receive an externally threaded annular nut 67 secured to an internally threaded opening 68. The internal annular nut 67 at the right end serves the same purposes as the matching annular nut 61 at the left end, i.e., it holds in place a reflecting cone 70, which engages an O-ring 72 and also engages IRE 44 peripherally near the right end of the IRE.

Figure 9:
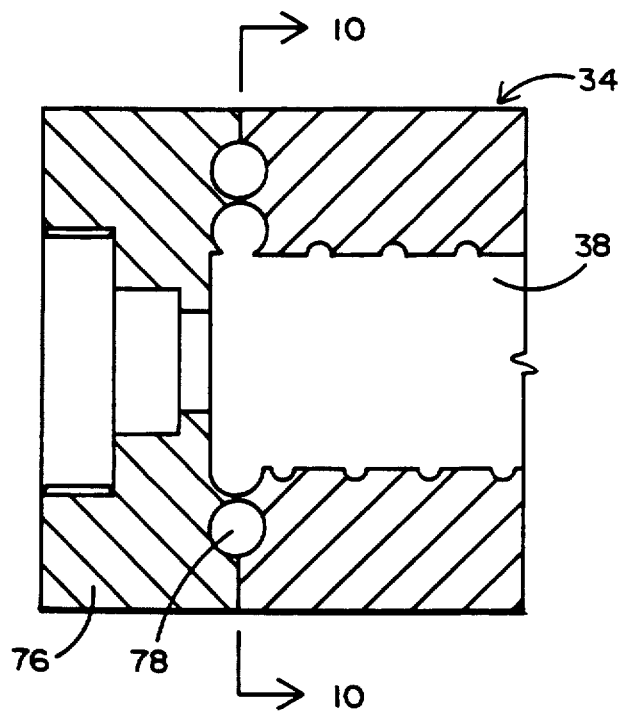
FIGS. 9 and 10 are cross-sectional views of a modified version of the invention, FIG. 10 being a section taken on line 10—10 of FIG. 9.
Figure 10:
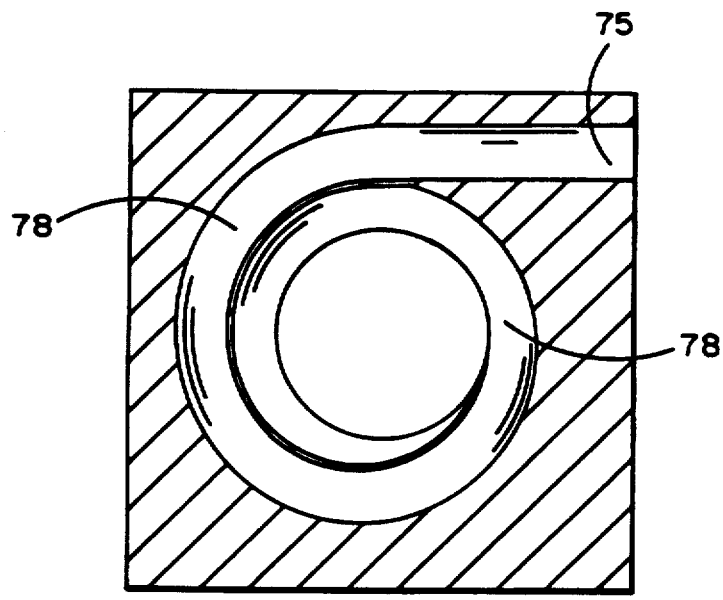
Figure 11:
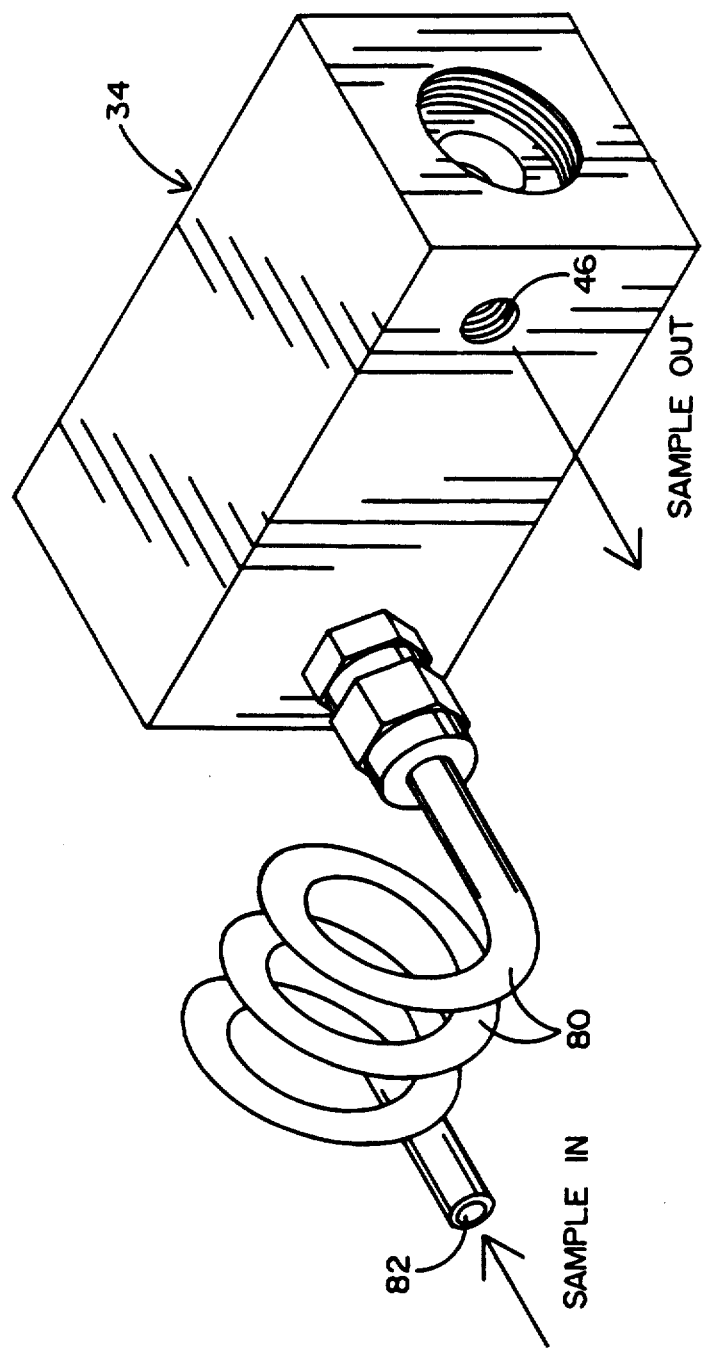
FIG. 11 is an isometric view of another modified version of the invention.

FIGS. 9-11 show two different modifications which provide added means for preventing damage to the IRE due to abrasive particles carried in the liquid sample stream. In some situations, it may be desirable to initiate the centrifugal process before the sample comes into contact with the IRE, in order to insure that any abrasive particles in the sample stream have started to migrate away from the IRE before having a chance to abrade it. This can be accomplished either by using a helical section of tubing in the input line, or by providing a region of the sample cell in which rotational flow is initiated prior to contacting the IRE.

In the embodiment shown in FIGS. 9 and 10, the liquid is introduced into a port 75 near the outer edge of an annular member 76 secured to one end of the sample cell housing. The incoming sample is forced to spiral inwardly in a passage 78, with increasing angular velocity as it flows into the main sample cell chamber 38. By the time it reaches this chamber, the particulate matter should be concentrated along the outer edge of the flow path, i.e., the side of the path away from the surface of the IRE.

FIG. 11 shows a less costly structure for causing centrifugal force to separate particles carried in the liquid sample stream before the stream reaches the sample chamber. The sample stream enters the chamber inlet port after traveling through a spiral conduit 80, which it enters at an opening 82. When the sample liquid reaches the sample chamber, any particles should be at the outer wall of the chamber. Therefore, they would not strike the IRE.

Figure 12:
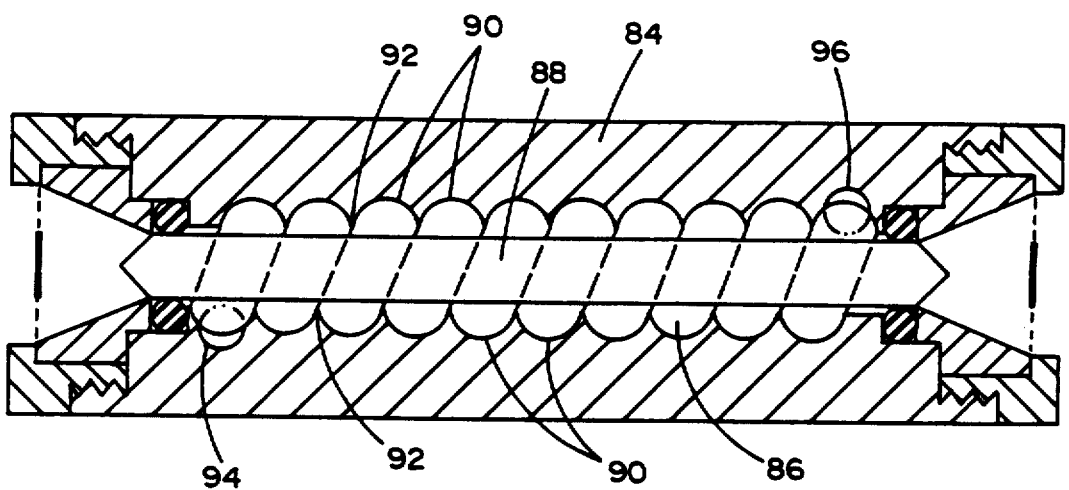
FIG. 12 is a cross-sectional view of yet another modified version of the invention.

FIG. 12 shows an embodiment which provides a much larger helical path for the sample. This enlarged helical path will ensure adequate helical motion of the sample, even when relatively viscous sample liquids are involved.

The use of offset input and output orifices is most effective when the samples involved are rapidly moving, nonviscous materials. This will be the case with a great many samples and will apply in most cases when the cell is being cleaned out, due to the non-viscous nature of most of the solvents that might be used.

However, when slow moving, relatively viscous samples are involved, the offset orifices will not be very effective. In this case, the assumption that a given molecule interacts only with the cell wall will not apply. Instead the behavior of a given molecule will be dominated by its interactions with all of its neighboring molecules. The fluid will be in a state approximating that of hydrostatic equilibrium. Any motion will simply take place in the direction of least resistance.

In the viscous case, just described, it is especially important to provide a means for insuring that the sample reaches every part of the cell and, in particular, insuring that the material in each region of the cell is continually being replaced by new material. This can be accomplished by the use of very pronounced "rifling," as shown in FIG. 12. In this figure, the gap between the IRE and the housing wall is much greater in the center of a groove than at the ridge between adjacent grooves.

In FIG. 12, a housing 84 has its longitudinal chamber 86 formed between the outer surface of an IRE 88 and a deep, continuous helical groove 90. The helical groove is similar to a deep rounded thread having separate turns of the helical groove separated only by a thin helical ridge 92. An input orifice is shown at 94, and an output orifice at 96.

Clearly, in FIG. 12, the bulk of the sample will be forced to move inside helical groove 90. As pressure is applied to the material in the deeply grooved chamber by new material entering the input orifice, most of the sample in a given region will flow in the direction of the helical groove 90. This is due to the fact that the cross sectional clear area for flow in this direction is much greater than for flow between the grooves. There will thus be a net flow in the direction of the helix, and virtually all of the material will be replenished in time.

From the foregoing description, it will be apparent that the apparatus and method disclosed in this application will provide the significant functional benefits summarized in the introductory portion of the specification.

The following claims are intended not only to cover the specific embodiments and methods disclosed, but also to cover the inventive concepts explained herein with the maximum breadth and comprehensiveness permitted by the prior art.

What is claimed is:

1. A sample cell structure in which a liquid sample is analyzed by means of radiation moving inside an internal reflecting element (IRE), comprising:
   a housing having a cylindrical chamber extending longitudinally therethrough;
   an IRE extending longitudinally through the chamber in the housing, said IRE having a circular cross-section;
   the annular space between the IRE and the cylindrical wall of the chamber constituting a sample chamber through which the liquid sample is caused to travel;
   an inlet port through which the liquid sample enters the chamber, said inlet port being located near one end of the IRE and being radially offset from the IRE in order to cause the incoming liquid stream to impact the chamber wall rather than the IRE;
   means for sealing the IRE at both ends to prevent sample leakage;
   an outlet port through which the liquid sample exits the chamber, said outlet port being located near the other end of the IRE; and
   a helical groove formed in the wall of the chamber having sufficient depth to cause a significant portion of the sample flow to move in the helical path provided by the groove.

2. The sample cell structure of claim 1 in which:
   the helical groove formed in the wall of the sample chamber fills a major portion of the annular space, in order to ensure that viscous samples will travel in the helical groove.

3. The sample cell structure of claim 1 which comprises:

particle separation means for causing the sample liquid to flow in a path which tends to separate solid particles carried by the liquid as a result of centrifugal force, in order to prevent such particles from striking the IRE.

4. The sample cell structure of claim 3 in which the particle separation means comprises a spiral flow path structure through which the entering sample liquid passes before it enters the sample chamber.

5. The sample cell structure of claim 4 in which both the entering sample stream and the exiting sample stream are caused to flow in directions essentially tangential to the cylindrical wall of the sample chamber.

6. A sample cell structure in which a liquid sample is analyzed by means of radiation moving inside an internal reflecting element (IRE, comprising:
- a housing having a cylindrical chamber extending longitudinally therethrough;
- an IRE extending longitudinally through the chamber in the housing, said IRE having a circular cross-section;
- the annular space between the IRE and the cylindrical wall of the chamber constituting a sample chamber through which the liquid sample is caused to travel;
- the wall of the sample chamber having a helical groove formed therein which is deep enough to force a major portion of the sample to travel along a helical path;
- an inlet port through which the sample enters the chamber, said inlet being located near one end of the IRE; and
- an outlet port through which the liquid sample exits the chamber, said outlet port being located near the other end of the IRE.

7. The sample cell structure of claim 6 which also comprises:

particle separation means for causing the sample liquid to flow in a path which tends to separate solid particles carried by the liquid as a result of centrifugal force, in order to prevent such particles from striking the IRE.

8. The sample cell structure of claim 6 in which both the entering sample stream and the exiting sample stream are caused to flow in directions essentially tangential to the cylindrical wall of the sample chamber.

9. A sample cell structure in which a liquid sample is analyzed by means of radiation moving inside an internal reflecting element (IRE), comprising:
- a housing having a cylindrical chamber extending longitudinally therethrough;
- an IRE extending longitudinally through the chamber in the housing, said IRE having a circular cross-section;
- the annular space between the IRE and the cylindrical wall of the chamber constituting a sample chamber through which the liquid sample is caused to travel;
- means for causing a liquid sample stream to enter into the space between the chamber wall and the IRE (a) in a direction tangential to the chamber wall, and (b) at a location near one end of the IRE;
- means for causing the liquid sample stream to exit from the space between the chamber wall and the IRE (a) in a direction tangential to the chamber wall, and (b) at a location near the opposite end of the IRE; and
- particle separation means comprising a spiral flow path structure through which the entering sample liquid passes before it enters the sample chamber.

* * * * *